Feb. 27, 1951 O. E. FELTEN Plant Pat. 1,005
STRAWBERRY PLANT
Filed Feb. 24, 1949
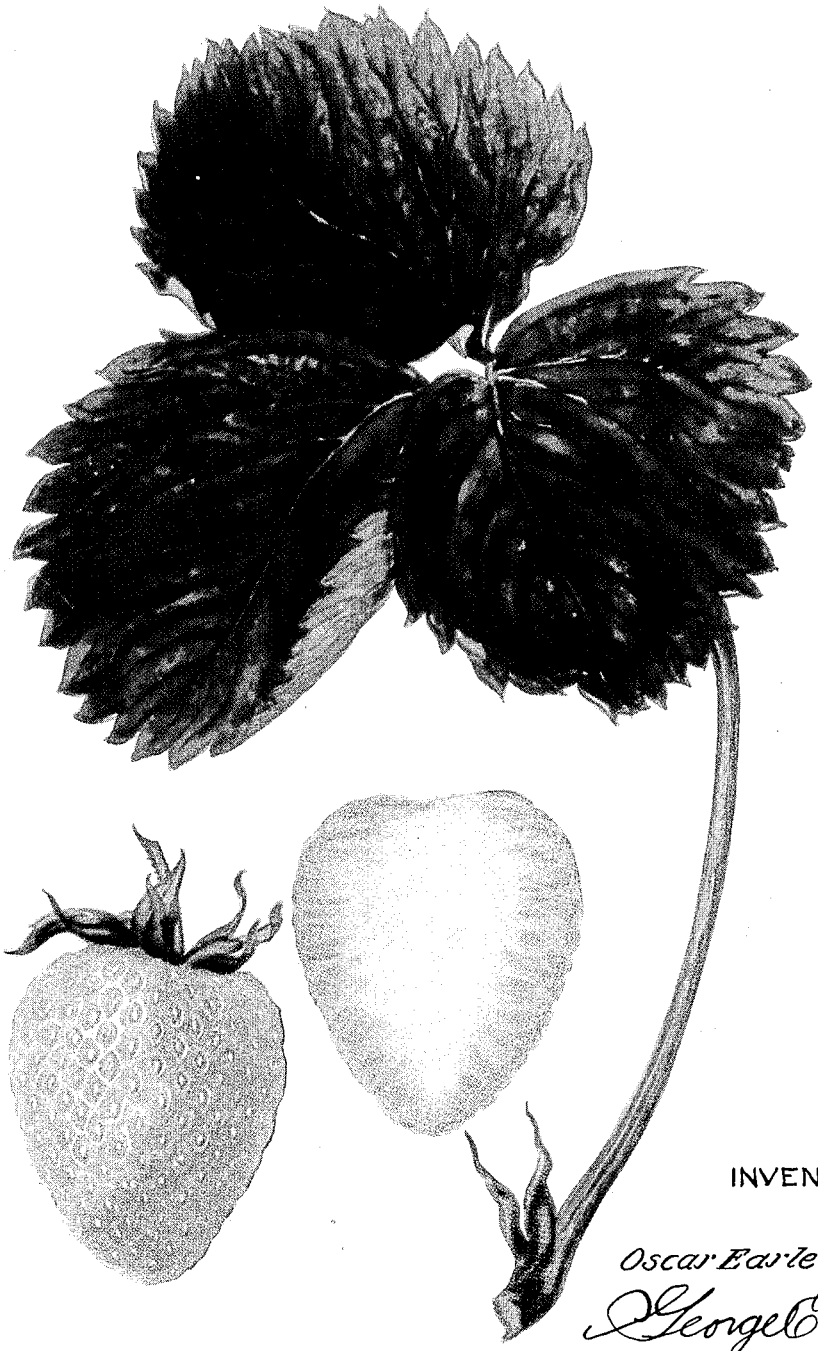
INVENTOR
Oscar Earle Felten
George E. Cook.
ATTORNEY Patented Feb. 27, 1951

Plant Pat. 1,005

UNITED STATES PATENT OFFICE 1,005

STRAWBERRY PLANT

Oscar Earle Felten, East Merchantville, N. J.

Application February 24, 1949, Serial No. 78,130

1 Claim. (Cl. 47—62)

My present invention relates to improvements in commercial strawberry plants. The object of my invention is the production of a commercial strawberry variety which is vigorous and healthy and produces a good crop of large berries of attractive appearance and superior flavor. These qualities have been accomplished in my new variety and it has been found excellent as a fresh berry on the market as well as having tested excellently for use as my frozen fruit.

The known variety most like my new variety is Premier, but there are many differences, chief of which are as follows:

1. My variety produces much larger berries.
2. The berries of my variety have a richer aroma and flavor.
3. The flavor of the berries of my new variety differs radically.
4. The berries of my variety ripen more evenly and without green tips.
5. The berries of my variety are always globe-conical, while those of Premier vary. Also the berries of my variety are thicker at the top.
6. The berries of my variety have no hard places such as are usually found in Premier.

Dorsett is another variety somewhat similar to my new variety, but differs chiefly as follows:

1. The fruit stems of my new variety are stronger, holding the berries upright much longer, thus keeping berries cleaner.
2. My variety is a more consistent producer of large berries throughout the season.
3. My variety does not make such a matted row as does Dorsett.
4. Ripening season of my variety is a little earlier than Dorsett.
5. My variety is more likely to set all its flowers into fruit.
6. The berry of my variety has a firmer texture yet is without hard spots.
7. The flavor of the berry of my variety differs greatly from that of Dorsett, mine having a sweet, spicy, pineapple-like quality not found in Dorsett. Likewise the aroma of the two berries differs.
8. The calyx of my variety is more adherent to the berry.
9. The flesh of the berry of my variety is darker red, particularly at the edges.

My new variety originated as a seedling of Felten seedling stock and is the result of inbreeding of unnamed Felten seedlings. It has been asexually reproduced by me in my nurseries in New Jersey for several years and the distinctive characteristics have been retained.

The illustrations accompanying these specifications show a leaf, a typical berry, and a longitudinal cross-section of a berry—all in approximately their true colors.

In the following detailed description of the plant and fruit of my new variety, color plate references indicate Ridgeway's Color Standards and Nomenclature, and other color names indicate the ordinary dictionary meaning of the term.

*The plant*

Type: Self-pollinating. Flowers "perfect."

Root system: Strong and vigorous.

Growth: Tall, strong, and upright. Runners fairly numerous; heavy, with long internodes. Plants large and well spaced in rows.

Production: Very heavy producer of large berries which retain their size throughout the season.

Disease resistance: No virus diseases have ever been noted and there is very little leafspot.

Frost resistance: Berries have not been affected by late frosts in the section where grown.

Foliage: Abundant. Large, usually trifoliate, each lobe measuring about 3 inches long by 2¾ inches wide. Leaflets are broadly oval in shape and sharply serrated. Color is medium green with only a small edging of bronze. *Leaf stems* ciliate, upright and 8 to 10 inches in length. Usually bronzed.

Fruit stems: Slightly shorter than leaf stems, each holding from 5 to 7 berries which ripen in rotation. Very strong, holding the berries well off the ground until about ripe, at which time they fall down by their weight. By being held upright so long the berries do not get embedded in the dirt and do not mildew.

*The fruit*

Season: Ripens early to midseason—about May 30 to June 7 being the height of their season in this territory.

Shape: Globe-conical.

Size: Large. Average berry measures 1¾ inches long and 5¼ inches in circumference both around the thickest part at the top and from top to apex.

Color: Bright red, almost Spectrum Red (Plate 1). Numerous yellow seeds or aichens are evenly distributed over the surface and slightly embedded.

Aspect: Bright and glossy. Ripens evenly with no green tips. Discolors very little for some days after becoming ripe.

Skin: Slightly tender but berry holds shape well.

Aroma: Sweet and spicy.

Calyx: Medium to large, with small hub; slightly embedded. Adheres well and stem snaps off easily, making it easy to retain calyx when picking. This of course is a very valuable feature commercially.

Flesh:

*Texture.*—Solid and firm, with fine texture and no hard places.

*Juiciness.*—Very juicy.

*Color.*—Deep rich color at edges, approximately the same as the outside color. This verges to lighter toward center. As shown in the illustration, a light streak divides the center of the berry from the outer segment. In a horizontal cross-section, this appears as a distinct ring and constitutes a slight break in the flesh when the berry is very ripe. Inside this ring the color is darker than that surrounding it but not so dark as the marginal area.

*Flavor.*—Very distinctive and difficult to describe; with the same qualities suggested by its aroma. Probably best described by saying it is sub-acid having rich aromatic strawberry flavor with a quality resembling the flavor of pineapple.

Having thus disclosed my invention, I claim:

The new and distinct variety of strawberry plant substantially as herein shown and described, characterized particularly by its strong and healthy growth; its strong, upright fruit stems; its consistent production throughout the season of large, globe-conical berries having an attractive color of skin and flesh, together with a distinctive rich, pineapple-like aroma and flavor; and its adherent calyx which snaps easily from the stem.

OSCAR EARLE FELTEN.

REFERENCES CITED

The following references are of record in the file of this patent:

U. S. Department of Agriculture Circular No. 257 of January 1933. "The Dorsett, Fairfax and Narcissa Strawberries."

U. S. Department of Agriculture Farmers' Bulletin No. 1043. "Strawberry Varieties in the United States."